US006335960B2

(12) United States Patent
Knigge et al.

(10) Patent No.: US 6,335,960 B2
(45) Date of Patent: *Jan. 1, 2002

(54) DETECTION OF VARIABLE MANUFACTURING TOLERANCE PACKAGES UTILIZING X-RAYS

(75) Inventors: Wayne I. Knigge, Maple Grove, MN (US); Brian A. Piotrowski, Aurora, IL (US)

(73) Assignee: General Mills, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/825,767

(22) Filed: Apr. 4, 2001

Related U.S. Application Data

(63) Continuation of application No. 09/420,163, filed on Oct. 18, 1999, now Pat. No. 6,215,845.

(51) Int. Cl.[7] .............................................. G01N 23/04
(52) U.S. Cl. ........................................... 378/57; 378/58
(58) Field of Search ............................. 378/57, 58, 87, 378/90, 62

(56) References Cited

U.S. PATENT DOCUMENTS

| | | | |
|---|---|---|---|
| 3,917,947 A | 11/1975 | Fenton | |
| 4,366,382 A | 12/1982 | Kotowski | |
| 4,430,568 A | 2/1984 | Yoshida et al. | |
| 4,788,704 A | 11/1988 | Donges et al. | |
| 5,056,124 A | * 10/1991 | Kakimoto et al. | ............. 378/57 |
| 5,202,932 A | 4/1993 | Cambier et al. | |
| 5,260,982 A | 11/1993 | Fujii et al. | |
| 6,023,497 A | * 2/2000 | Takahashi et al. | ............. 378/57 |
| 6,047,041 A | * 4/2000 | Ellinger | ....................... 378/58 |
| 6,215,845 B1 | * 4/2001 | Knigge | ........................ 378/57 |

FOREIGN PATENT DOCUMENTS

| | | | |
|---|---|---|---|
| EP | 0273370 A | 6/1988 | |
| JP | 06314949 A | 8/1994 | |

* cited by examiner

*Primary Examiner*—Robert H. Kim
*Assistant Examiner*—Irakli Kiknadze
(74) *Attorney, Agent, or Firm*—John A. O'Toole; Douglas J. Taylor; Alan D. Kamrath

(57) ABSTRACT

Detection of components (22–24) missing from sealed packages (16) is accomplished by combining a multiplicity of electrical outputs representing the mass in volumes of the package (16) and comparing the combined value with a standard value for packages (16) including all components (22–24). In the preferred form, the mass is represented by the absorption of x-rays, with the packages (16) being conveyed on a conveyor (18) between an x-ray radiator (12) generating a fan-shaped x-ray beam (14) and a line array (20) of individual detectors (20a, 20b, etc.). The detectors (20a, 20b, etc.) detect radiation after passing through the package (16) and provide a numerical electrical signal equal to the amount of radiation detected. If the sum of the multiplicity of numerical electrical signals is less than the standard value, the package (16) is rejected from the conveyor (18) by a rejection device (30).

20 Claims, 3 Drawing Sheets

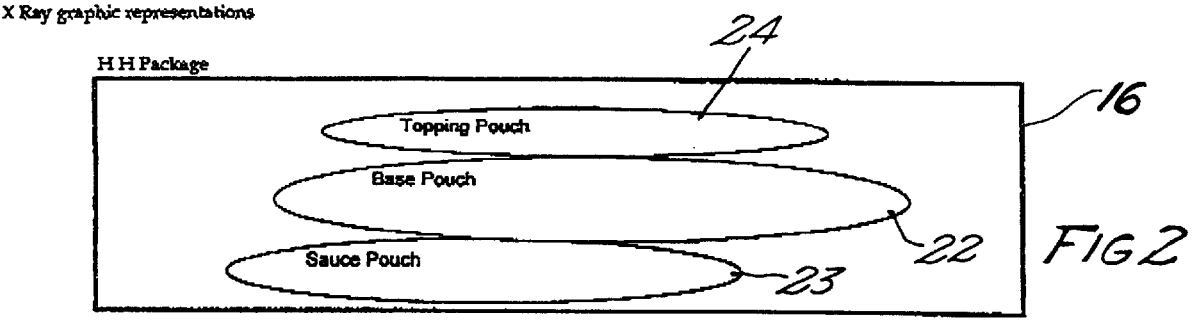
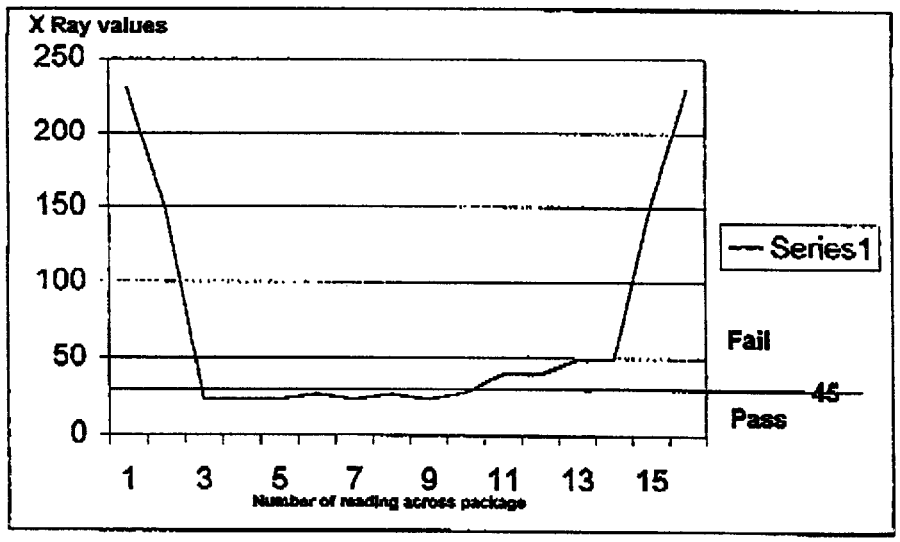

X Ray graphic representations
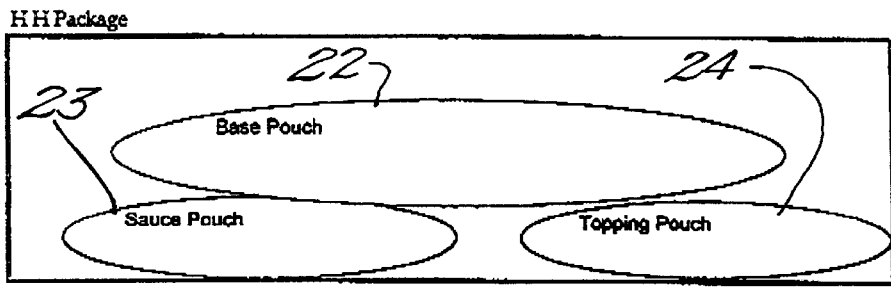
FIG 5
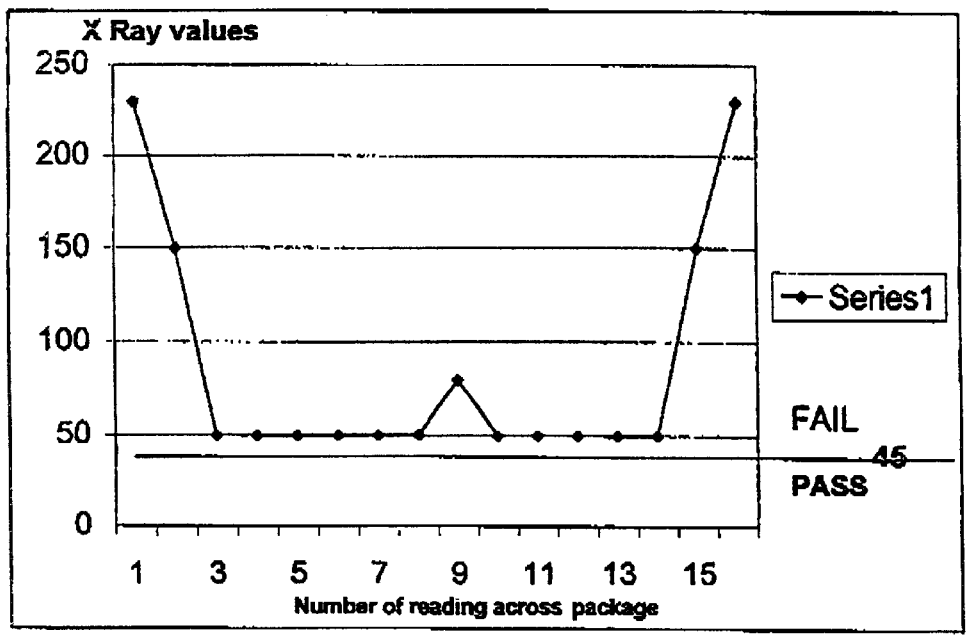
FIG 6
FIG 7

DETECTION OF VARIABLE MANUFACTURING TOLERANCE PACKAGES UTILIZING X-RAYS

CROSS REFERENCE

The present application is a continuation of U.S. application Ser. No. 09/420,163 filed Oct. 18, 1999, now U.S. Pat. No. 6,215,845.

BACKGROUND

The present invention generally relates to the detection of missing components in a package, particularly to an x-ray scanner and processing system for detecting missing components in a package, and specifically to an x-ray scanner and processing system for detecting missing components which can have a variety of positions within a package.

A number of products are marketed in the form of multiple components which are included within a sealed package, with the consumer removing the components from the package at a location remote from the point of purchase and combining those components to form the final product. As the components are located within the package, the manufacturer as well as the consumer are unable to verify whether or not the package includes all components until after the package is opened. As many products are now mechanically packaged, packages where all the components are not there, where multiple components are present, and like deficiencies will be created depending upon machinery reliability. As such packaging errors are a major cause of consumer complaints especially when packages do not include all the necessary components to produce the final product, there exists a need for systems to detect whether the proper components are present in the package without requiring the opening of such packages.

One manner of such detection is by weighing the final package after sealing. This suffers from several shortcomings including reliability of correctly weighing the individual packages as they are being conveyed on a conveyor. Similarly, the weight of a component may be such that if one component were omitted (or a duplicate included), the package including the remaining components would be within the range of weights for the package including all components manufactured within the normal manufacturing tolerances.

Also, the components could be manufactured including identifiers which can be sensed outside of the package. However, it can then be appreciated that this has limitations in the number of identifiers which can be included in a single package and still be separately identifiable, typically requires extra manufacturing steps, and results in false negatives as the components could be present in the package but either the identifiers were omitted or could not be sensed from outside of the package.

X-ray scanning systems have had wide commercial success in the detection of contaminants in a package. Typical applications would be detecting metal in food products, bone portions in fillets, lumps or clumps in powdered or semi fluid components, or the like. Although prior x-ray scanning systems have been utilized for detecting missing components, use of x-ray scanning systems were generally limited to packages where the components are in a consistent position within the packages. Example packages would include egg cartons, TV dinners, and the like.

X-ray scanning detection systems are desirable for several reasons including but not limited to they do not require use of identifiers, do not require any modifications to the production line upstream from the detection system, do not leave marks or have the potential of damaging the sealed package and the like. Thus, a need exists for an x-ray scanning system which is able to detect which packages include one or more missing components where the components can have a variety of arrangements or positions within the package and which do not generate a substantial number of false negatives.

SUMMARY

The present invention solves this need and other problems in the field of package x-ray detection systems and methods by, in the most preferred form, comparing the combined value of a multiplicity of outputs of radiation detectors corresponding to areas of a package with a standard value for a package including all desired components and rejecting any packages having package values that do not meet the standard value. In the most preferred form, the multiplicity of outputs are generated by moving the packages on a conveyor between a fan shaped beam x-ray radiator and a row of detectors.

It is thus an object of the present invention to provide a novel x-ray scanner and processing system.

It is further an object of the present invention to provide such a novel x-ray scanner and processing system which is not orientation dependent.

It is further an object of the present invention to provide such a novel x-ray scanner and processing system especially useful for detecting missing components in a package where the components can have a variety of positions or arrangements inside of the package.

It is further an object of the present invention to provide such a novel x-ray scanner and processing system substantially eliminating the generation of false negatives.

Other objects and advantages of the invention will become apparent from the following detailed description of an illustrative embodiment of this invention described in connection with the drawings.

BRIEF DESCRIPTION OF THE DRAWINGS

The illustrative embodiment may best be described by reference to the accompanying drawings where:

FIG. 2 shows a cross sectional view of a representative package scanned by the system of FIG. 1.

FIG. 3 shows an array of illustrative numerical outputs generated by the system of FIG. 1 scanning a package of the type represented by FIG. 2.

FIG. 4 shows a graphical depiction generated by prior systems scanning a package of the type represented by FIG. 2.

FIG. 5 shows a cross sectional view of another representative package scanned by the system of FIG. 1.

FIG. 6 shows an array of illustrative numerical outputs generated by the system of FIG. 1 scanning a package of the type represented by FIG. 5.

FIG. 7 shows a graphical depiction generated by prior systems scanning a package of the type represented by FIG. 5.

Figure 1:
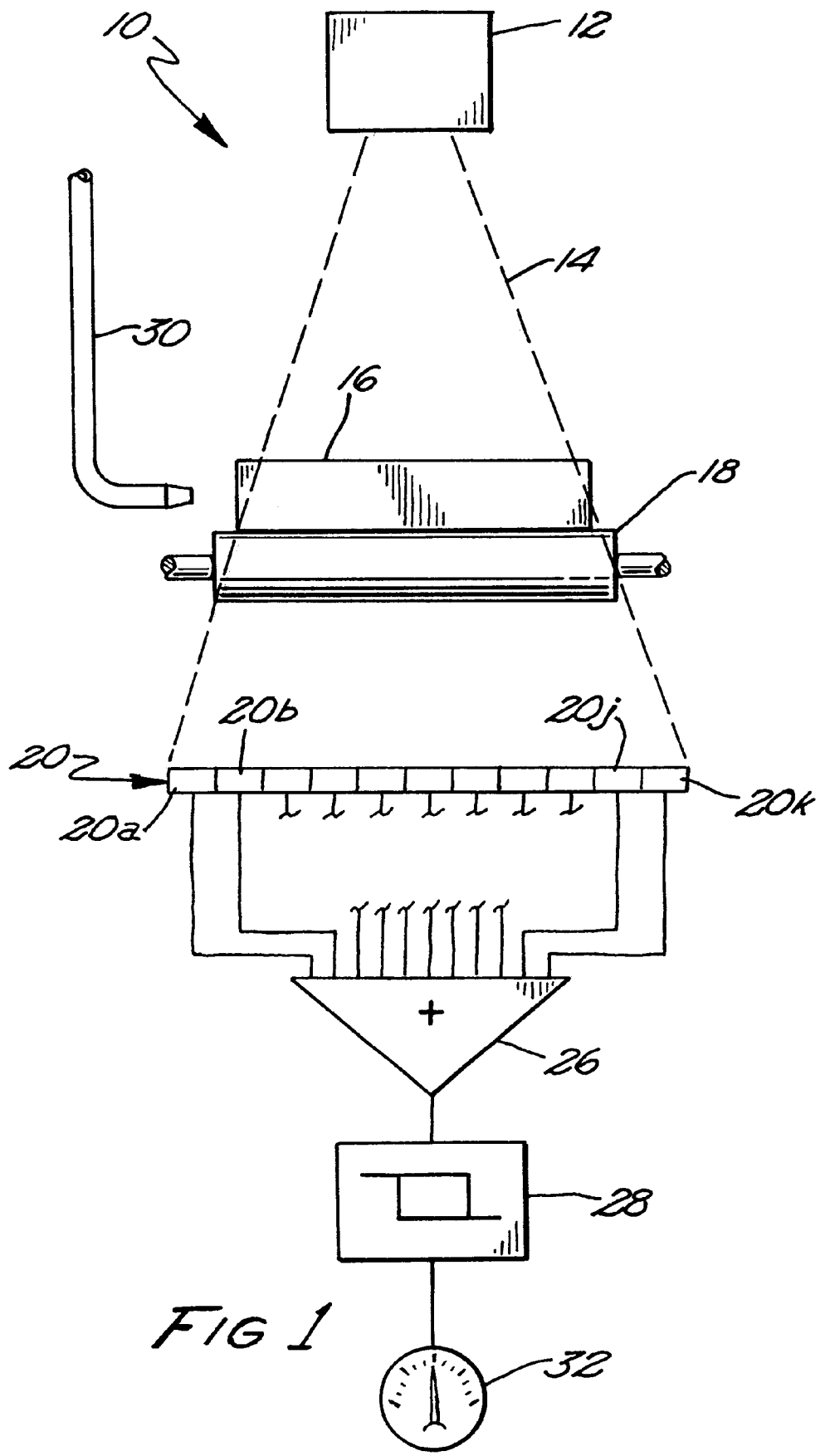
FIG. 1 shows a diagrammatic view of an x-ray scanner and processing system according to the preferred teachings of the present invention.

All figures are drawn for ease of explanation of the basic teachings of the present invention only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

DESCRIPTION

An x-ray scanner and processing system according to the preferred teachings of the present invention is shown in the drawings and generally designated 10. System 10 includes an x-ray radiator 12 which generates energy waves in the form of a fan-shaped x-ray beam 14 encompassing and irradiating packages 16 on a conveyor 18. The plane of the fan shaped x-ray beam 14 is perpendicular to the conveying direction, with the conveying direction extending out of the plane of the drawing. The radiation passing through package 16 and conveyor 18 is received by a line or row array 20 comprised of a plurality of individual detectors 20a, 20b, etc. For purposes of explanation, it will be assumed that eleven individual detectors 20a, 20b, etc. extend across the width of package 16 on conveyor 20. In actuality, the number of individual detectors 20a, 20b, etc. is in the order of 256 to 512. Likewise, for purposes of explanation, a numerical reference is given to the output of each of the individual detectors 20a, 20b, etc., with the larger number indicating that a greater amount of radiation is being received by the individual detectors 20a, 20b, etc. In the following description, when package 16 is not positioned between x-ray radiator 12 and array 20, the maximum output of the individual detector 20a, 20b, etc. is 255. It can then be appreciated that if package 16 is positioned between radiator 12 and array 20, the output of the individual detectors 20a, 20b, etc. will be less than 255 depending upon the particular composition to the material in the plane of x-ray beam 14. As an example, if metal were positioned in between radiator 12 and any particular detector 20a, 20b, etc. in the plane of beam 14, the output of those particular detectors 20a, 20b, etc. would be 0 as no radiation would be detected. However, it can be appreciated that the numerical value is entirely arbitrary and a matter of choice. As an example, the value could be based upon the amount of radiation blocked, with the numerical value of 0 indicating no radiation is being blocked and a positive number such as but not limited to 100 indicating that 100% of the radiation is being blocked. The same principles are involved no matter what numerical values are assigned to the outputs of the individual detectors 20a, 20b, etc.

It should further be appreciated that beam 14 is generated in cycles by radiator 12 and in the most preferred form is generated at approximately 700 cycles/second. Thus, as package 16 is conveyed on conveyor 18 and moved between radiator 12 and array 20, individual detectors 20a, 20b, etc. generate a multiplicity of outputs corresponding to distinct areas of package 16. In the most preferred form, package 16 takes about one half second to pass entirely through the plane of beam 14 such that 350 readings are made across package 16.

It should then be appreciated that system 10 as described thus far is of a conventional design (see as an example U.S. Pat. No. 4,788,704). Historically, such systems 10 were utilized to detect contaminants in package 16. As an example, if the output of one or more individual detectors 20a, 20b, etc. indicated that no radiation was being detected at any time that package 16 including food was in the plane of beam 14, package 16 was rejected because such an indication indicated the undesired presence of metal. Such rejection typically is in the form of removal from conveyor 18 by suitable means 30 such as but not limited to removal by air jets, grabbing or pushing arms, moveable conveyor sections or the like. In addition to metals, system 10 could be utilized to detect other contaminants such as but not limited to the presence of a bone in a fillet, or the like, where the amount of radiation being detected by the individual detectors 20a, 20b, etc. was less than the range of amount normally detected by the individual detectors 20a, 20b, etc. Use of system 10 for detecting contaminants in packages 16 has historically been very successful in these applications.

In addition to the presence of unwanted components, the next progression of system 10 was to detect the absence of missing components. Specifically, packages 16 often include multiple components 22, 23, and 24. As an example, component 22 could be a pouch including a base such as pasta, component 23 could be a pouch including a sauce such as a tomato sauce, and component 24 could be a pouch including a topping such as a cheese. Prior to the present invention, system 10 utilized the same threshold detection in determining whether components were missing as when contaminants were present. Specifically, it was assumed that if the components 22–24 were present, the amount of radiation being detected would be less than when one or more components 22–24 were missing. Thus, if the amount of radiation that was detected by detectors 20a, 20b, etc. was less than a threshold amount, it was assumed that the components 22–24 were present. Use of system 10 in this manner is fairly successful if components 22–24 and package 16 had consistent positioning, in other words everything in package 16 was regimented and stationary relative to package 16. As an example, packages 16 in the form of egg cartons including individual components 22–24 in the form of eggs held in their own compartments and always passing through the plane of beam 14 in the same orientation can be successfully scanned by system 10 to detect the absence of one or more individual eggs from package 16. Specifically, if one or more individual eggs were missing from package 16, the radiation detected by array 20 would be greater than for packages 16 where individual eggs are not missing and could be rejected by system 10. In this regard, detection of missing components 22–24 having consistent positioning inside of package 16 can be successfully accomplished using a threshold mode of operation where if a threshold amount of radiation reduction is detected, it can be assumed that the components 22–24 are there, and additionally if a greater amount of radiated reduction is detected, it can be assumed that a contaminant is present.

It can be appreciated that if packages 16 passed through the plane of beam 14 in a different orientation, the radiation reduction detected by the individual detectors 20a, 20b, etc. would not be the same between the individual packages 16. However, the orientation of packages 16 entering system 10 can be easily mechanically controlled to be consistent. The problem arises when components 22–24 can have a variety of positions or are allowed to move inside of package 16. Specifically, the radiation reduction detected by the individual detectors 20a, 20b, etc. would not be the same with components 22–24 at various positions inside of package 16.

With this as background, the method of detecting missing components 22–24 from package 16 according to the teachings of the present invention can be explained and differentiated from prior methods in connection with a package 16 including three components 22–24. For purposes of explanation, it is desirable to have components 22–24 in a vertical stacked arrangement on conveyor 18 in the position shown in FIG. 2 with base component 22 located intermediate components 22 and 24 and with component 23 located closest to conveyor 18. It can be appreciated that when mechanically positioned in and sealed within package 16, components 22–24 will be in the desired arrangement about 90% of the time. However, about 10% of the time, for whatever reason, components 22–24 do not have the desired orientation. An example of another possible orientation is shown in FIG. 6 wherein components 23 and 24 are in a side-by-side arrangement adjacent to conveyor 18 and component 22 is stacked on and straddles components 23 and 24.

FIG. 3 represents an array of a multiplicity of numerical outputs of the individual detectors 20a, 20b, etc. as package 16 including components 22–24 in the arrangement of FIG. 2 passes through the plane of beam 14. It should be appreciated that the array is merely illustrative for the sake of simplicity as only 11 readings are provided in each row across the width of package 16 corresponding to 11 individual detectors 20a, 20b, etc. when in actuality a multiple of times that number of individual detectors 20a, 20b, etc. are provided. Similarly, only 16 readings are provided in each column across the length of package 16 corresponding to the number of cycles of radiator 12 when in actuality a multiple of times that number of cycles are provided. Based upon an x-ray value of 255 where no reduction in radiation is detected and considering the lowest value detected by the individual detectors 20a, 20b, etc. in the line array 20 or considering the value detected by an individual detector 20a, 20b, etc. generally located in the center of the width of package 16, a reduction in the radiation is detected as the paperboard or other material forming package 16 passes through the plane of beam 14, which reduction is indicated by the numerical output of 230. Further reduction in radiation is detected as component 23 passes through the plane of beam 14, and then components 22 and 23 pass through the plane of beam 14, and then all three components 22–24 pass through the plane of beam 14. It can be appreciated that the reduction in detected radiation will be the greatest when the plane of beam 14 simultaneously passes through all three components 22–24, with the actual reduction of radiation being dependent upon several factors including the particular consistency of the material within components 22–24, the particular thickness of components 22–24 and the like, with the greatest reduction in radiation in the example having a numerical output of 24. As package 16 continues to travel through the plane of beam 14, there is less reduction in radiation as the end of component 23 passes through the plane of beam 14, and lesser still as the end of component 24 passes through the plane of beam 14, and even lesser still as the end of component 22 passes through the plane of beam 14 and beam 14 again only passes through the material forming package 16. It should be appreciated that the individual detectors 20a, 20b, etc. do not have the same numerical outputs, but the radiation detected by any particular detector 20a, 20b, etc. and the numerical output will be dependent on the particular position of the particular detector 20a, 20b, etc. in array 20, with the detectors 20a, 20b, etc. adjacent the edges of package 16 and components 22–24 typically experiencing less radiation reduction than detectors 20a, 20b, etc. in the center of package 16.

FIG. 4 represents a graphical representation that would be displayed utilizing prior methods for the numerical outputs of the array of FIG. 3. In particular, the lowest numerical value (representing the greatest reduction in radiation) is plotted for each successive reading as package 16 passes through beam 14. As this numerical value is below a threshold value indicated as the numerical value of 45 in FIG. 4, this particular package 16 would pass the scanning test of system 10 and would not be rejected thereby. In this regard, the numerical value does not pass a minimal value such as being equal to 0 which would indicate the presence of a contaminant, which would be a reason that system 10 would reject package 16.

FIG. 6 represents an array of numerical outputs of individual detectors 20a, 20b, etc. as package 16 which includes components 22–24 in the arrangement of FIG. 5 passes through the plane of beam 14 utilizing the same parameters as set forth for FIG. 3. Based upon an x-ray value of 255 where no reduction in radiation is detected and considering the lowest value detected by the individual detectors 20a, 20b, etc. in the line array 20 or considering the value detected by an individual detector 20a, 20b, etc. generally located in the center of the width of package 16, a reduction in the radiation is detected as the paperboard or other material forming package 16 passes through the plane of beam 14, which reduction is indicated by the numerical output of 230. Further reduction in radiation is detected as component 23 passes through the plane of beam 14, and then components 22 and 23 pass through the plane of beam 14. However, as package 16 continues to travel through the plane of beam 14, there is less reduction in radiation as the end of component 23 passes through the plane of beam 14 and beam 14 passes only through component 22. Greater reduction in radiation is again detected as the end of component 24 passes through the plane of beam 14 and beam 14 passes through both components 22 and 24. There is less reduction in radiation as the end of component 22 passes through the plane of beam 14 and lesser still as the end of component 24 passes through the plane of beam 14 and beam 14 again only passes through the material forming package 16. In this example, beam 14 never passes simultaneously through components 22–24 and thus the reduction in radiation of package 16 of FIG. 6 is lesser than the maximum reduction in detected radiation of package 16 of FIG. 2.

FIG. 7 represents a graphical representation that would be displayed utilizing prior methods for the numerical outputs of the array of FIG. 6. In particular, the lowest numerical value (representing the greatest reduction in radiation) is plotted for each successive reading as package 16 passes through beam 14. As this numerical value is always above a threshold value indicated as the numerical value of 45 in FIGS. 4 and 7, this particular package 16 would fail the scanning test of system 10 and would be rejected by the rejection means 30 of system 10. However, package 16 of FIG. 5 includes all 3 components 22–24 , and system 10 would have provided a false negative. In actual practice, about one half of the 10% of the packages 16 which contain all 3 components 22–24 but not in the desired arrangement of FIG. 2 are falsely rejected as not including all components 22–24. This is an amount which makes system 10 utilizing prior methods commercially unacceptable for detecting missing components 22–24 in packages 16.

The present invention is the recognition that the outputs of the individual detectors 20a, 20b, etc. of array 20 can be utilized in a manner which was not previously considered and/or which was considered inoperable to arrive at a commercially acceptable method for detecting missing components 22–24 in packages 16. In particular, it was recognized that although the manner that radiation is reduced is dependent upon the arrangement of components, the total amount of radiation which is absorbed by components 22–24 as well as the material forming package 16 is generally dependent upon mass of the particular components and the amount of mass does not change with the arrangement of components 22–24. According to the methods of the present invention, the multiplicity of electrical outputs of individual detectors 20a, 20b, etc. is combined to arrive at a combined value by suitable means diagramatically designated in FIG. 1 as 26. It can then be appreciated that the sum of all the values of each of the individual detectors 20a, 20b, etc. of array 20 of all of the successive readings as package 16 passes through beam 14 provides a representation of the combination of the electrical values of radiation absorbed by components 22–24 and the material forming package 16 located in discreet volumes represented by individual blocks in the arrays of FIGS. 3 and 6, with the amount of radiation being absorbed being directly related or in other words a representation of the mass of components 22–24 and package 16 in those discreet volumes.

According to the teachings of the present invention, the combined value is compared with a standard value by suitable means diagramatically designated in FIG. 1 as 28. The standard value is identified by scanning and obtaining combined values of packages 16 including all components 22–24 within the normal manufacturing tolerance ranges. In this regard, the standard value would be in the form of a range for acceptable products. The standard value could be variable and float according to the particular operating parameters including but not limited to the environment temperature, relative humidity, and the like.

As shown in FIG. 3, the total sum of values of the numerical outputs of the individual detectors 20a, 20b, etc. for all of the successive readings as package 16 of FIG. 2 passes through beam 14 is 22398 which is equal to the total sum of values of the numerical outputs of the individual detectors 20a, 20b, etc. for all of the successive readings as package 16 of FIG. 7 passes through beam 14, even through the numerical outputs for particular detectors 20a, 20b etc. are not the same in the arrays of FIGS. 3 and 6. The total sum of values is then set to encompass normal manufacturing tolerances from a desired package 16 including the desired weight and makeup of components 22–24.

There are several reasons why it is believed that persons skilled in the art did not consider utilizing the total amount of radiation which is absorbed as a criteria in testing packages 16. First, this method of the present invention does not provide testing for contaminants, the initial reason why system 10 was developed. In particular, although the numerical outputs of particular detectors 20a, 20b, etc. for particular readings could be beyond the prior thresholds, the total sum of values could be within an acceptable range for the desired total. Thus, it is believed that the mindset of those skilled in the art was that this criteria would not useful in testing packages for contaminants and thus would not be useful in testing packages per se. Although recognizing this deficiency, the method of the present invention is a recognition that x-ray system 10 can be utilized in a different manner to achieve results which were not previously considered or considered inoperable. In this regard, testing for contaminants in addition to the method of the present invention is contemplated including but not limited to the utilization of prior x-ray contamination methods in parallel with the methods of the present invention and even utilizing the same outputs of the individual detectors 20a, 20b, etc. but for multiple purposes.

Additionally, the method of the present invention does not lend itself to graphical depiction as do the prior methods as depicted in FIGS. 4 and 7. In particular, although a single value for each successive reading of array 20 has significance and can be easily graphically displayed, the successive readings of array 20 has no significance in the method of the present invention as only the total value of the readings representing the total amount of radiation absorbed has significance. Thus, graphical depiction is not needed, and only a counter type gauge 32 showing the total value of the readings is the only type of visual indication necessary, if desired.

Further it should be appreciated that unlike mass, absorption of x-rays is position dependent. As an example, the absorption of x-rays is subject to a Bernoulli Equation as to distance. It can then be appreciated that the distance of components 22–24 from radiator 12 are different in packages 16 shown in FIGS. 2 and 5, and thus the rate of absorption of x-rays by components 22–24 as sensed by the individual detectors 20a, 20b, etc. in the packages 16 of FIGS. 2 and 5 will be different. Due to this non-linear relationship and the belief that this would prevent any meaningful use of an indication of the total amount of x-ray absorption, its use prior to the present invention had not been considered or had been considered inoperable by persons skilled in the art. However, it was discovered that in the ranges necessary to operate system 10 according to the methods of the present invention that a person skilled in computer processing can easily develop an algorithm which converts the values of detectors 20a, 20b, etc. to approximate a linear relationship to allow the total sum of values to have a practical and meaningful significance in the method of the present invention in the detection of missing components 22–24 in package 16. The method of the present invention is then proceeding opposite to conventional thinking in the field of x-ray detection systems.

Although not illustrated, it can be clearly appreciated that if one or more components 22–24 were missing from package 16, the prior method would not reach its threshold value and the total sum of values would not be within the acceptable range of the method of the present invention. Thus, both methods would result in a rejection of package 16 which omitted one or more components 22–24 by any suitable means such as but not limited to an air jet diagramatically designated in FIG. 1 as 30.

Similarly, system 10 can be utilized in the method of the present invention to detect if individual components 22–24, although present, are not within the desired manufacturing weight tolerances. In particular, it should be appreciated that if components 22, 23, or 24 are present in a greater amount than desired, the radiation detected will be less and if present in a lesser amount than desired, the radiation detected will be greater. This variation (outside of a normal tolerance range) can be detected by system 10 according to the teachings of the present invention. Thus, the line check weigher scales utilized in prior production lines could be eliminated utilizing system 10 of the present invention and especially for small weight components could have greater reliability than prior conveyor scales.

Similarly, in the most preferred form system 10 could be utilized to check for contaminants in parallel with the methods for checking for missing components of the present invention. Thus, metal detectors and other component checking equipment could be eliminated.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. Method for detecting if a package is within a range of manufacturing tolerances comprising: generating a multiplicity of electrical outputs representing the mass in volumes of the package; combining the multiplicity of electrical outputs to arrive at a combined value; identifying a standard value of a package within the range of manufacturing tolerances; comparing the combined value with the standard value; and rejecting the package where the combined value does not meet the standard value.

2. The method of claim 1 wherein generating the multiplicity of electrical outputs comprises: radiating the package with an x-ray beam generated by an x-ray radiator; and detecting radiation passing through the package at spaced locations on the opposite side of the package than the x-ray radiator.

3. The method of claim 2 wherein the package is on a conveyor when radiated.

4. The method of claim 3 wherein the package is radiated by a fan shaped x-ray beam; wherein the radiation is detected by a line of detectors; and wherein the package is moved between the radiator and line of detectors to generate the multiplicity of electrical outputs.

5. The method of claim 4 wherein the multiplicity of outputs corresponds to the total volume of the package.

6. The method of claim 5 further comprising: displaying the combined value.

7. The method of claim 6 wherein the electrical outputs are numerical values.

8. The method of claim 7 wherein the electrical outputs represent the amount of radiation detected.

9. The method of claim 1 wherein the package is radiated by a fan shaped x-ray beam; wherein the radiation is detected by a line of detectors; and wherein the package is moved between the radiator and line of detectors to generate the multiplicity of electrical outputs.

10. The method of claim 1 wherein the multiplicity of outputs corresponds to the total volume of the package.

11. The method of claim 1 wherein the electrical outputs are numerical values.

12. The method of claim 1 wherein the electrical outputs represent the amount of radiation detected.

13. The method of claim 1 wherein identifying the standard value comprises identifying the standard value of the package within the range of manufacturing weight tolerances.

14. System for detecting if a package is within a range of manufacturing tolerances comprising, in combination: means for radiating the package with an energy wave which is absorbable by the package; means for detecting the energy passing through the package and for generating a multiplicity of electrical outputs representing the mass in volumes in the package; means for combining the multiplicity of electrical outputs to arrive at a combined value; means for comparing the combined value with a standard value for a package within the range of manufacturing tolerances; and means for rejecting the package where the combined value does not meet the standard value.

15. The system of claim 14 wherein the radiating means comprises an x-ray radiator.

16. The system of claim 15 wherein the x-ray radiator radiates a fan-shaped x-ray beam; and wherein the detecting means comprises a line of individual detectors, with the package being moved between the x-ray radiator and the line of detectors to generate the multiplicity of electrical outputs.

17. The system of claim 16 further comprising, in combination: a conveyor for conveying the package between the radiating means and the detecting means, with the rejecting means removing the package from the conveyor.

18. The system of claim 16 wherein the detecting means detects the level of energy remaining after passing through the package.

19. The system of claim 14 wherein the detecting means detects the level of energy remaining after passing through the package.

20. The system of claim 14 wherein the comparing means comprises means for comparing the combined value with the standard value for a package within the range of manufacturing weight tolerances.

* * * * *